(12) United States Patent
Forsyth et al.

(10) Patent No.: US 10,552,553 B2
(45) Date of Patent: Feb. 4, 2020

(54) CAPILLARY PRESSURE ANALYSIS FOR PETROPHYSICAL STATISTICAL MODELING

(71) Applicant: Saudi Arabian Oil Company, Dhahran (SA)

(72) Inventors: David Forsyth, Dhahran (SA); Yusuf Ziya Pamukcu, AlKhobar (SA); Nasr-Eddine Hammou, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 377 days.

(21) Appl. No.: 14/828,029

(22) Filed: Aug. 17, 2015

(65) Prior Publication Data

US 2017/0053046 A1 Feb. 23, 2017

(51) Int. Cl.
*G06F 17/50* (2006.01)
*G06F 17/18* (2006.01)
(Continued)

(52) U.S. Cl.
CPC ....... *G06F 17/5009* (2013.01); *G01N 15/088* (2013.01); *G01N 33/24* (2013.01); *G06F 17/18* (2013.01); *G01V 9/00* (2013.01)

(58) Field of Classification Search
CPC ........ G01N 15/088; G01N 33/24; G01V 9/00; G06F 17/18; G06F 17/5009
See application file for complete search history.

(56) References Cited

U.S. PATENT DOCUMENTS 4,790,180 A 12/1988 Sinnokrot
5,828,981 A 10/1998 Callender et al.
(Continued)

FOREIGN PATENT DOCUMENTS

WO 2010/022851 3/2010
WO 2015/021088 2/2015

OTHER PUBLICATIONS

Comisky, Joseph Thomas, Kent Newsham, Jay Alan Rushing, and Thomas Alwin Blasingame. "A comparative study of capillary-pressure-based empirical models for estimating absolute permeability in tight gas sands." In SPE Annual Technical Conference and Exhibition. Society of Petroleum Engineers, 2007.*

(Continued)

*Primary Examiner* — Aniss Chad
(74) *Attorney, Agent, or Firm* — Fish & Richardson P.C.

(57) ABSTRACT

A multiple curve capillary pressure data set derived from a core sample is discriminated into groups of similar curves representing similar pore structure groups. Primary reservoir development controlling factors (RDCFs) are identified for each pore structure group and a set of capillary pressure type curves are created for each pore structure group to statistically characterize saturation-pressure response. Data is processed from a core sample log to derive identified RDCFs from the log data. A preliminary reservoir development designation log is derived by applying cutoffs to the log-based RDCFs and a preliminary saturation distribution equivalent to the preliminary reservoir development designation log is obtained by applying the capillary pressure type curves. A capillary pressure type uncertainty envelope is compared with saturation measurements from the log. The modelled saturation from the average capillary pressure type curve is recalculated to generate an optimized reservoir development designation.

17 Claims, 12 Drawing Sheets

(10 of 12 Drawing Sheet(s) Filed in Color)

(51) Int. Cl.
  *G01N 33/24*   (2006.01)
  *G01N 15/08*   (2006.01)
  *G01V 9/00*    (2006.01)

(56) References Cited

U.S. PATENT DOCUMENTS

| | | | |
|---|---|---|---|
| 6,490,531 | B1 | 12/2002 | Goglin et al. |
| 6,833,699 | B2 * | 12/2004 | Galford ............. G01V 3/32 324/303 |
| 7,072,809 | B2 | 7/2006 | Egermann et al. |
| 7,333,892 | B2 | 2/2008 | Egermann et al. |
| 8,301,428 | B2 * | 10/2012 | Lukyanov ............. E21B 43/00 703/10 |
| 8,645,070 | B2 | 2/2014 | Hanson et al. |
| 8,868,390 | B2 | 10/2014 | Enchery |
| 9,121,256 | B2 * | 9/2015 | Fournier ............. E21B 49/00 |
| 9,671,525 | B2 * | 6/2017 | Al-Ibrahim ............. G01V 9/02 |
| 2012/0143578 | A1 | 6/2012 | Fournier |
| 2013/0131989 | A1 | 5/2013 | Buiting et al. |
| 2013/0297273 | A1 | 11/2013 | Altundas et al. |
| 2014/0019054 | A1 | 1/2014 | De Prisco et al. |
| 2014/0136116 | A1 | 5/2014 | Banian et al. |

OTHER PUBLICATIONS

Xu, Chicheng, and Carlos Torres-Verdín. "Petrophysical rock classification in the Cotton Valley tight-gas sandstone reservoir with a clustering pore-system orthogonality matrix." Interpretation 2, No. 1 (2014): T13-T23.*

Schmitt, Mayka, Celso P. Fernandes, José AB da Cunha Neto, Fabiano G. Wolf, and Viviane SS dos Santos. "Characterization of pore systems in seal rocks using nitrogen gas adsorption combined with mercury injection capillary pressure techniques." Marine and Petroleum Geology 39, No. 1 (2013): 138-149.*

Comisky, Joseph Thomas, Michael Santiago, Bruce McCollom, Aravinda Buddhala, and Kent Edward Newsham. "Sample size effects on the application of mercury injection capillary pressure for determining the storage capacity of tight gas and oil shales." In Canadian unconventional resources conference. Society of Petroleum Engineers, 2011.*

International Search Report and Written Opinion of the International Searching Authority issued in International Application No. PCT/US2015/058217 dated Jun. 20, 2016; 11 pages.

International Preliminary Report on Patentability in International Application No. PCT/US2015/058217 dated Feb. 20, 2018, 8 pages.

Gulf Cooperation Council Examination Report issued in GCC Application No. 2016-31044 on May 21, 2018, 3 pages.

Gulf Cooperation Council Examination Report issued in GCC Application No. 2016-31044 on Nov. 11, 2018, 4 pages.

* cited by examiner

CAPILLARY PRESSURE ANALYSIS FOR PETROPHYSICAL STATISTICAL MODELING

BACKGROUND

Several techniques exist to find, analyze, or predict subterranean reservoirs of hydrocarbons, natural gas, water, and/or other substances. For example, capillary pressure analysis can be performed on an actual rock sample from a reservoir well core sample. The capillary pressure analysis can provide concrete information about the porosity and permeability of types of rock present in the rock sample and to provide useful information about rock characteristics within a reservoir formation. Actual rock sample analysis is normally very expensive and time consuming. Another less expensive and faster method is to use saturation modeling approaches with rock type and assigned permeability characteristics. Current saturation modeling approaches assume that the petrophysical properties of rocks can be defined entirely from lithologic log data. Based on the rock type or assigned permeability characteristics, water saturation of the rock can be predicted. Measured water saturation from log data is used purely for comparison purposes.

SUMMARY

The present disclosure describes methods and systems, including computer-implemented methods, computer-program products, and computer systems for using capillary pressure analysis with Reservoir Development Controlling Factors (RDCFs) to improve predication of rock types/characteristics and creation of representative saturation height models.

A multiple curve capillary pressure data set derived from a core sample is discriminated into groups of similar curves representing similar pore structure groups. Primary reservoir development controlling factors (RDCFs) are identified for each pore structure group and a set of capillary pressure type curves are created for each pore structure group to statistically characterize saturation-pressure response. Data is processed from a core sample log to derive identified RDCFs from the log data. A preliminary reservoir development designation log is derived by applying cutoffs to the log-based RDCFs, and a preliminary saturation distribution equivalent to the preliminary reservoir development designation log is obtained by applying the capillary pressure type curves. A capillary pressure type uncertainty envelope is compared with saturation measurements from the log. The modelled saturation from the average capillary pressure type curve is recalculated to generate an optimized reservoir development designation.

Other implementations of this aspect include corresponding computer systems, apparatuses, and computer programs recorded on one or more non-transitory computer-readable media/storage devices, each configured to perform the actions of the methods. A system of one or more computers can be configured to perform particular operations or actions by virtue of having software, firmware, hardware, or a combination of software, firmware, or hardware installed on the system that in operation causes or causes the system to perform the actions. One or more computer programs can be configured to perform particular operations or actions by virtue of including instructions that, when executed by data processing apparatus, cause the apparatus to perform the actions.

For example, one computer-implemented method includes: discriminating a multiple curve capillary pressure data set derived from a core sample into groups of similar curves representing similar pore structure groups; identifying the primary RDCFs for each pore structure group; creating a set of capillary pressure type curves for each pore structure group to statistically characterize saturation-pressure response for each pore structure group; processing data from a log corresponding to the core sample to derive the identified RDCFs from the log data; deriving a preliminary reservoir development designation log by applying cutoffs to the log-based RDCFs; obtaining a preliminary saturation distribution equivalent to the preliminary reservoir development designation log by applying the capillary pressure type curves; comparing a capillary pressure type uncertainty envelope with saturation measurements from the log; and recalculating the modelled saturation from the average capillary pressure type curve to generate an optimized reservoir development designation.

The foregoing and other implementations can each optionally include one or more of the following features, alone or in combination:

A first aspect, combinable with the general implementation, wherein the capillary pressure data set is determined from a subset of core plug data selected from a pre-existing set of core plug data.

A second aspect, combinable with any of the previous aspects, wherein a pore structure group is a group of curves associated with rock structures having similar porosities or permeabilities.

A third aspect, combinable with the general implementation, wherein the created capillary pressure type curves reduce the number curves characterizing each pore structure group using at least one of average, maximum, minimum, or standard deviation.

A fourth aspect, combinable with any of the previous aspects, wherein a Multimin probabilistic analysis technique uses a mineral model and measured physical characteristics within the log to predict mineral compositions associated with the log.

A fifth aspect, combinable with the general implementation, wherein uncertainty in the preliminary saturation distribution is defined by an envelope of maximum and minimum saturations and a standard deviation.

A sixth aspect, combinable with any of the previous aspects, comprising using an inverse petrophysical modeling technique with a full set of capillary pressure type curves to assess whether a saturation range associated with the defined reservoir development designation groupings of the reservoir development designation log is inconsistent with the measured log saturation.

The subject matter described in this specification can be implemented in particular implementations so as to realize one or more of the following advantages. First, actual capillary pressure data can be used to drive the saturation statistics for the reservoir model without simplification of capillary pressure data functions. Second, results can be obtained more quickly and with a better representation of the reservoir properties than other techniques such as applying neural net technology to raw log data. Third, saturation data can be characterized directly and statistically without the need for a transfer function. Fifth, the creation of reservoir geological models can be enhanced, for example, by reducing the time to populate reservoir properties and/or by improving modeling of saturation uncertainties. Sixth, models with improved accuracy can be generated that have a significant impact on the placement of wells and/or for the design of accurate and appropriate field development plans. Seventh, an internally consistent rock model can link permeability to Reservoir Development Designations (RDDs) and saturation. Eighth, statistical uncertainties in both the RDD and measured saturations can be incorporated in the model to provide an improved model which honors the statistics. Ninth, incorporating statistics in the saturation modeling allows uncertainties in geological volume calculation to be better quantified. Other advantages will be apparent to those of ordinary skill in the art.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

The patent or application file contains at least one drawing executed in color. Copies of this patent or patent application publication with color drawing(s) will be provided by the Patent and Trademark Office upon request and payment of the necessary fee.

Like reference numbers and designations in the various drawings indicate like elements.

DETAILED DESCRIPTION

Figure 1:
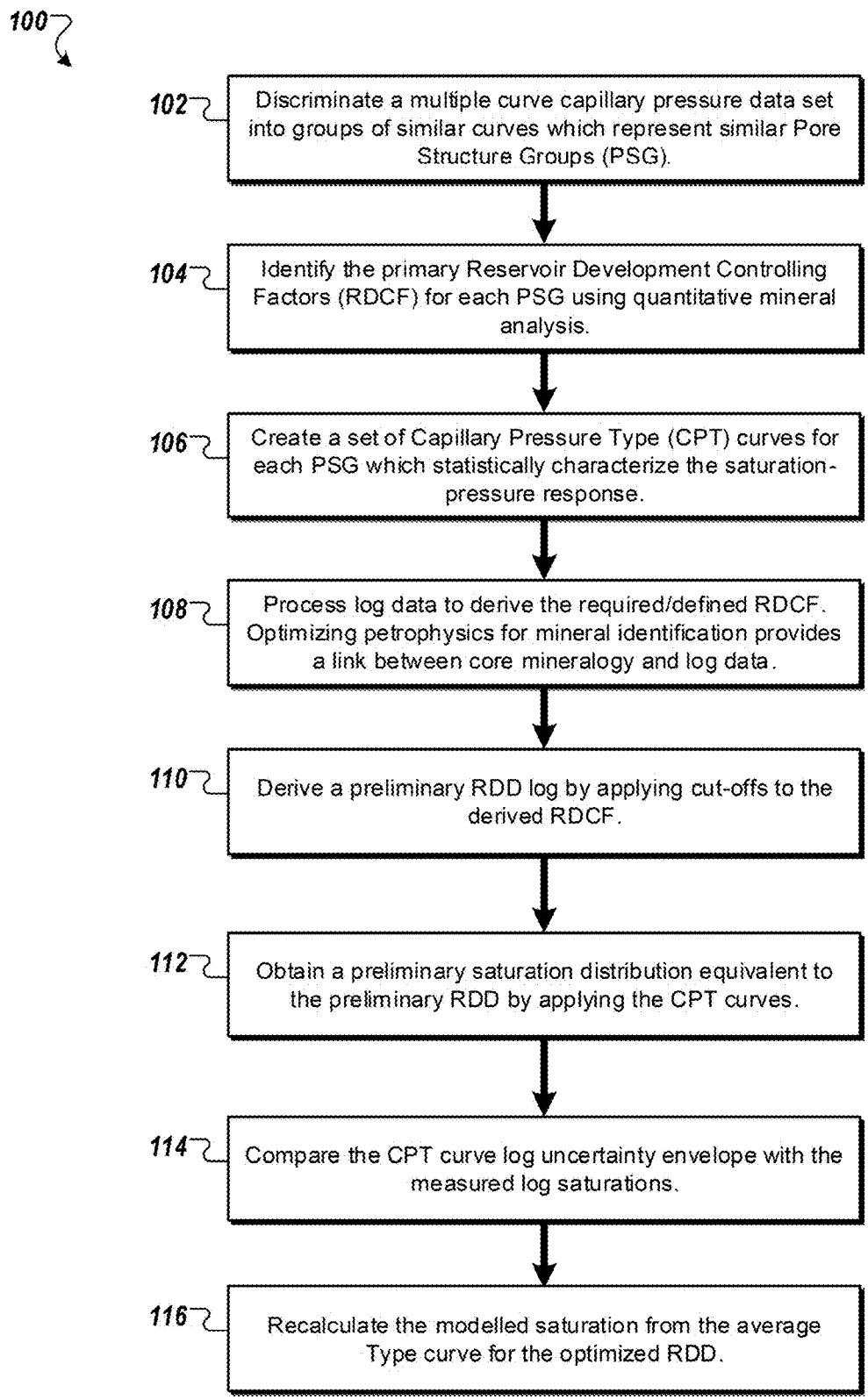
FIG. 1 illustrates a method 100 for characterizing reservoir properties using capillary pressure analysis with Reservoir Development Controlling Factors (RDCFs), according to an implementation.

This disclosure generally describes methods and systems, including computer-implemented methods, computer-program products, and computer systems, for using capillary pressure analysis with Reservoir Development Controlling Factors to improve predication of rock types/characteristics and creation of representative saturation height models.

The following description is presented to enable any person skilled in the art to make and use the invention, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

Several techniques exist to find, analyze, or predict subterranean reservoirs of hydrocarbons, natural gas, water, and/or other substances. For example, capillary pressure analysis can be performed on an actual rock sample from a reservoir well core sample. The capillary pressure analysis can provide concrete information about the porosity and permeability of types of rock present in the rock sample and to provide useful information about rock characteristics within a reservoir formation. Actual rock sample analysis is normally very expensive and time consuming. Another less expensive and faster method is to use saturation modeling approaches with rock type and assigned permeability characteristics. Current saturation modeling approaches assume that the petrophysical properties of rocks can be defined entirely from lithological log data. Based on the rock type or assigned permeability characteristics, water saturation of the rock can be predicted.

Capillary pressure analysis is a technique used to determine some properties of an actual sample of reservoir rock (e.g., from a core sample). For example, in some cases, a Mercury Injection Capillary Pressure (MICP) analysis is used, in which part of the technique includes injecting mercury into the rock sample. MICP analysis can provide information about the porosity and/or permeability of the rock sample, such as pore size, pore structure, and/or the ability of the pores to hold gas, oil, water, etc. The MICP analysis can generate a large number of measurement curves, and typically a single representative curve is generated from the set of curves that is used to estimate the porosity and/or permeability of the rock sample. The porosity and/or permeability results can be used to determine characteristics of the rock sample. For example, the type, quantity, and/or relative fraction of material present in the rock sample can be estimated. This information from the MICP analysis can provide information about reservoir formations that can be used, for example, to improve well placement and/or inform reservoir development plans. The information is also typically used to confirm results taken from log data.

At a high level, this disclosure is drawn to integrating core analysis data with log data to improve the prediction of rock types/characteristics and creation of representative saturation height models. In an example implementation, lithological log data and measured saturation data can be integrated to provide a consistent measure of reservoir rock types/characteristics. The technique described in this disclosure can be used not only to confirm log data but also to use the log data together with MICP analysis to improve the accuracy of determining rock types/characteristics in a formation. In some implementations, the output from this process can be incorporated directly in reservoir and geological models. Though the present disclosure describes a technique with respect to MICP analysis, the general technique can also be used with other types of analysis or other measurement techniques. For example, one additional area is in the identification of encroached water zones in mature reservoirs. Encroached water can be identified by comparing theoretical saturation distributions predicted by the model with the actual saturations measured in the well. Where the well oil saturations are low compared with the model can be indicative of encroached water zones.

The disclosed technique includes discriminating multiple MICP curves from multiple rock sample analyses into meaningful groups. Each group of capillary pressure curves can have specific associated physical characteristics and/or properties, and some of the specific physical characteristics and/or properties associated with each group can be determined.

The physical characteristics that determine the curve groups are referred to as Reservoir Development Controlling Factors (RDCFs). For example, similar curves could be grouped by RDCFs based on the mineral composition of the rock samples associated with the curves. Many possible RDCFs can be used alone or in combination, such as porosity, mineral composition, quartz content, grain size, permeability, and/or other factors. Each RDCF and associated curve grouping can be determined, for example, by a statistical analysis of the RDCF and curves. For each curve grouping, a set of type curves can be created. Each type curve in the set represents a statistical property such as the maximum, minimum, mean, and/or standard deviation of the curve data of the curve grouping. As an example, the maximum type curve and minimum type curve for a grouping can determine a range for a physical property associated with that grouping. In an example implementation, grouped capillary pressure data can define a saturation range based on the statistics for the capillary pressure data for that grouping. For this implementation, grouping statistics can define a range for the expected saturations for a type of rock.

Log data can then be analyzed with respect to the curve groupings to divide the log data into Reservoir Development Designations (RDDs) with different characteristics from poor to good reservoir quality. A RDD category is a rock type grouping where capillary pressure shows similar characteristics and forms a tighter grouped subset of the whole capillary data set. These subsets reflect variation in reservoir quality and ideally can be related to log measurable RDCF. In particular, the RDCFs can be used to partition the logged interval into an equivalent set of RDDs. For example, saturation measurements within log data can be categorized into RDDs according to which curve and curve statistics they most closely correspond. In some cases, a feedback loop is incorporated in which the measured log data is compared against the capillary pressure curve characteristics and the RDD designation is adjusted based on the comparison. A revised model saturation curve can then be calculated from the revised RDD. In this manner, RDD can be defined and refined using a modelled range of expected saturations based on saturation statistics derived from core capillary data. This statistical characterization for the modelled saturations can be compared with the measured log measured saturations. Thus, the RDD can be refined to improve the initial RDD. The revised RDD can be used to define the statistical range for permeabilities and water saturations in reservoir models.

FIG. 1 illustrates a method 100 for characterizing reservoir properties using capillary pressure analysis with Reservoir Development Controlling Factors according to an implementation. For clarity of presentation, the description that follows generally describes method 100 in the context of FIGS. 2A-D, 3A-B, 4A-B, 5-6, 7A-B, and 8-11. However, it will be understood that method 100 may be performed, for example, by any other suitable system, environment, software, and hardware, or a combination of systems, environments, software, and hardware as appropriate (e.g., the computer system described in FIG. 11 below). In some implementations, various steps of method 100 can be run in parallel, in combination, in loops, and/or in any order.

At 102, a set of capillary pressure data with multiple curves is discriminated into groups of curves. In some cases, a subset of core plug data can be selected from a preexisting set of core plug data, and the set of capillary pressure data can be determined based on the subset. The subset can be selected from the preexisting set using statistical techniques, selected manually, selected randomly, or selected using other techniques. In some cases, the subset of core plug data can include capillary pressure data. The subset of core plug data can be selected, for example, based on a range of observed porosities and/or permeabilities. In some cases, capillary pressure analysis can be performed on the plugs corresponding to the plugs in the subset to generate capillary pressure data corresponding to the subset. Capillary pressure analysis can be performed on the physical plugs corresponding to elements in the core data subset. For example, capillary pressure analysis can be performed on a whole plug or an end piece of a plug. The capillary pressure analysis can be performed via a suitable technique such as a mercury injection technique, a porous plate technique, a centrifuge technique, or another technique. In this manner, the capillary pressure analysis data from the core data subset can be a representative set of capillary pressure data including multiple analysis curves.

Figures 2A, 2B:
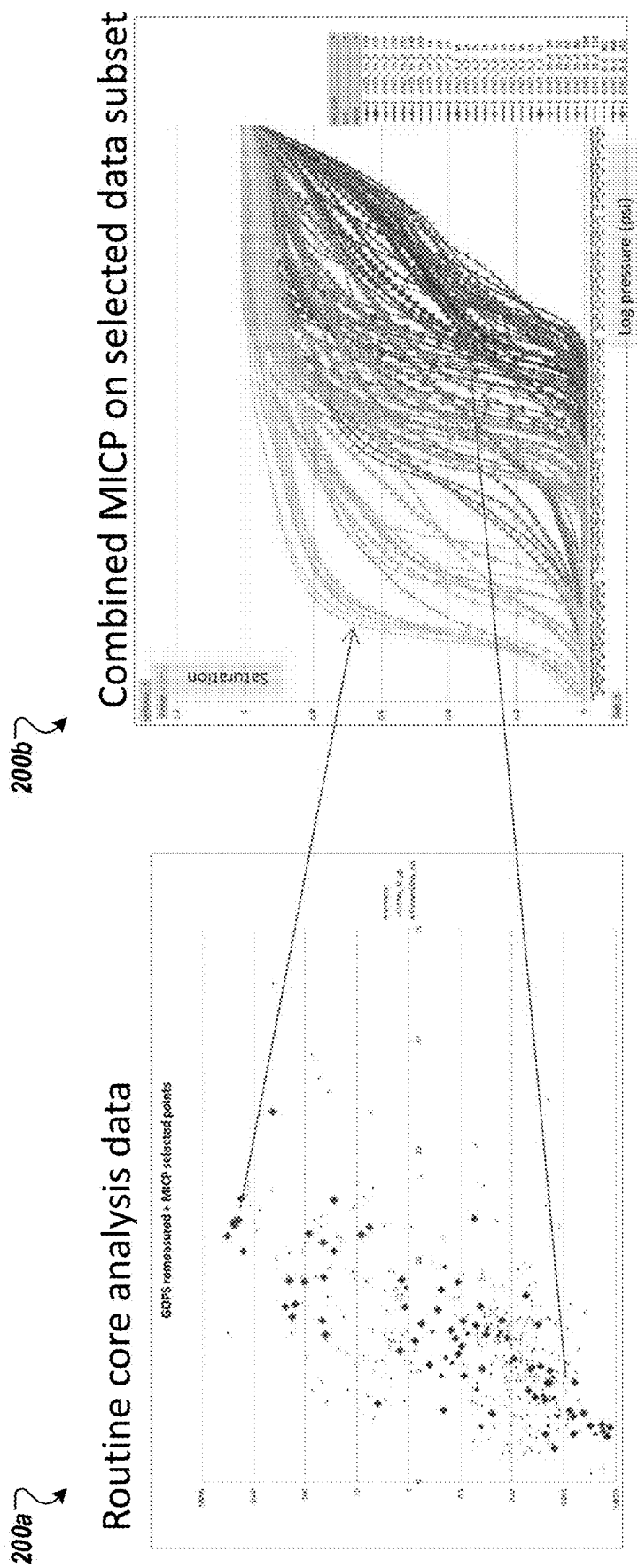
FIG. 2A illustrates a plot of an example set of core plug data, according to an implementation.
FIG. 2B illustrates a plot of an example combined set of capillary pressure data, according to an implementation.

Turning to FIGS. 2A-2D, FIG. 2A illustrates a plot 200a of an example set of core plug data from which a subset can be selected for capillary pressure analysis, according to an implementation. FIG. 2B illustrates a plot 200b of an example combined set of capillary pressure data generated from capillary pressure analysis on the subset of core plugs. Each curve in plot 200b is capillary pressure data corresponding to a capillary pressure analysis from an individual core plug. In the example shown in FIG. 2B, the combined capillary pressure data is generated from Mercury Injection Capillary Pressure (MICP) analysis of the plugs.

Returning to 102 in FIG. 1, the capillary pressure data set is discriminated into a number of curve groups based on curve similarity. Each group includes curves with similar shapes, values, or other characteristics. The number of groups can be determined from the characteristics of the capillary pressure data set. For example, the capillary pressure data set can be discriminated into two groups, three groups, four groups, or another number of groups. The groups can be generated using statistical or mathematic techniques, manually, based on visual similarity, and/or using other techniques. As each group has different overall characteristics (e.g., shape, entry pressure, etc.), each group can correspond to a different Pore Structure Group (PSG). A PSG is a group of curves that is associated with rock structures having similar porosities and/or permeabilities.

Figures 2C, 2D:
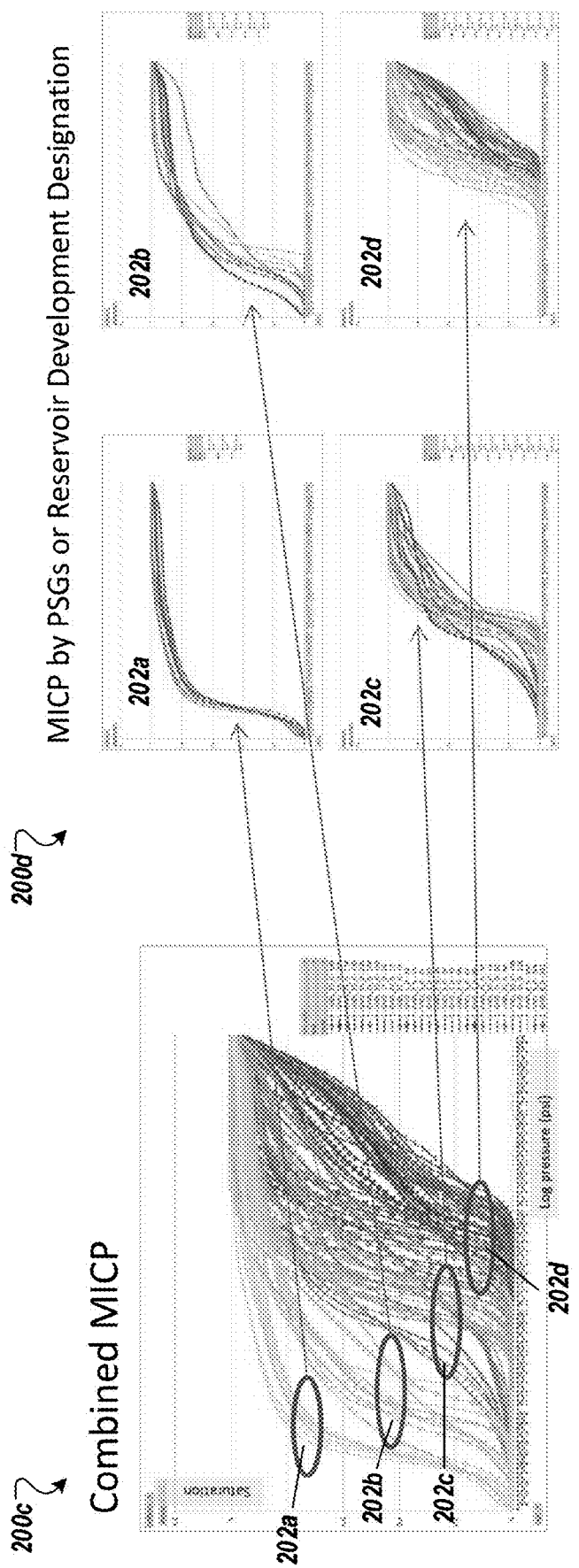
FIG. 2C illustrates an example plot of the combined capillary pressure data curves with example groups of curves designated, according to an implementation.
FIG. 2D illustrates an example multiple plot with the individual example groups and the respective curves within each group, according to an implementation.

Turning to FIGS. 2C-2D, FIG. 2C illustrates an example plot 200c of the combined capillary pressure data curves with example groups of curves 202a-d designated. FIG. 2D illustrates an example multiple plot 200d with the individual example groups 202a-d and the respective curves within each group 202a-d. It will be appreciated that the respective curves in each group 202a-d have similar shapes and values.

Returning to FIG. 1, from 102, method 100 proceeds to 104. At 104, quantitative mineral analysis can be performed on plugs to identify the primary Reservoir Development Controlling Factors (RDCF) for the groups. The RDCF are the quantitative and differentiating mineral characteristics associated with each group. For example, each group can correspond to a different mineral fraction, porosity, permeability, grain size, quartz volume, and/or other characteristics that can represent RDCF. In some implementations, other RDCFs could include: 1) degrees of matrix dissolution as a result of post depositional diagenesis; 2) post deposition cementation; 3) clay development and type of clay; 4) heavy oil or tar deposition; 5) post production scale or salt precipitation; 6) condensate banking; and 7) pore size and pore throat indices. As the curves within each group have similar characteristics, the groups can correspond to different PSGs, and thus the groups can also have one or more distinguishing RDCFs. One or more plugs from each group can be quantitatively analyzed and compared with plugs from other groups to identify one or more RDCFs. For example, routine core analysis data, capillary pressure data, quantitative mineral data, and/or grain size data can be integrated to identify the one or more RDCFs. In some cases, a primary RDCF can be identified as the main controlling RDCF that determines group discrimination. Furthermore, based on the core analysis, each curve group can be associated with a different Reservoir Development Designation (RDD) characterizing formation properties.

Figures 3A, 3B:
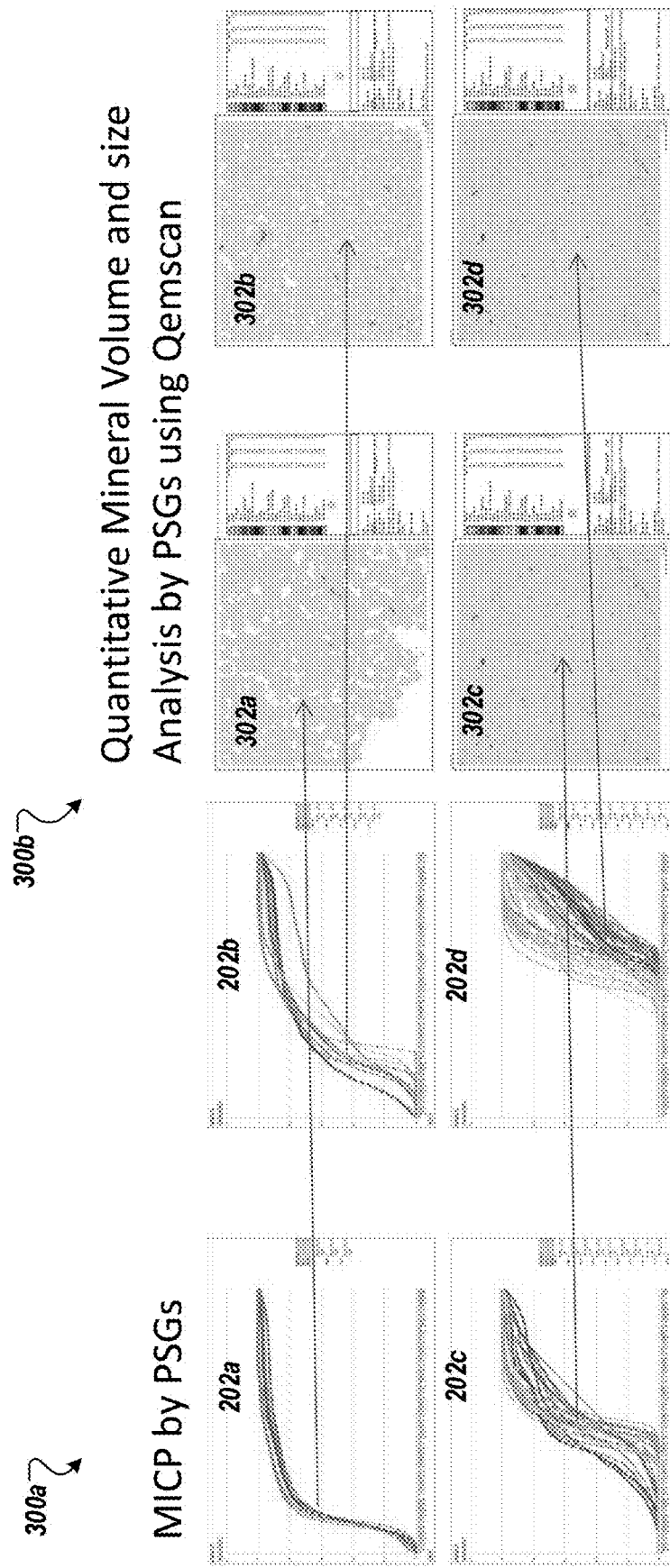
FIG. 3A illustrates a multiple plot with example groups, according to an implementation.
FIG. 3B illustrates analysis with example corresponding quantitative mineral analyses, according to an implementation.

Turning to FIG. 3A, FIG. 3A illustrates a multiple plot 300a with example groups 202a-d, and FIG. 3B illustrates analysis 300b with example corresponding quantitative mineral analyses 302a-d for a representative plug within each group, according to an implementation. For example, the analysis 302a associated with group 202a shows a relatively low quartz volume fraction, and the analysis 202d associated with group 302d shows a relatively high quartz volume fraction. In this manner, comparison between curves 202a-d and corresponding analyses 302a-d show that a high quartz volume fraction measured from a quantitative mineral analysis can group the capillary pressure curves into typical response and poor/non-reservoir groupings. Similarly, the porosity-permeability for the groups can be discriminated into a high permeability trend for the high quartz samples and a low permeability trend for the low quartz volume factor samples. In FIG. 3B, the characteristics change from a high quartz, well-sorted, large grain rock to rock with smaller grains and being less sorted. The high permeable trend is associated with the large grains. The poorer reservoir developed intervals are associated with finer rock fabric and less sorted grains. This reflects the distribution of finer wind-blown material in nature in desert environments where clays and feldspars, which are known to destroy reservoir properties, tend to be dominant. For the example shown in FIGS. 3A-B, quartz volume and grain size/sorting can be identified as a primary RDCF. Other RDCFs can also be identified and considered. For example, analysis of the example groups 202a-d indicates porosity is of secondary importance in determining the permeability characteristics of each group 202a-d. In other cases, other primary RDCF can be identified for groups using quantitative analysis, as described previously. Returning to FIG. 1, from 104, method 100 proceeds to 106.

At 106, a set of Capillary Pressure Type (CPT) curves can be generated for each curve group. The CPT curves can statistically characterize the capillary pressure data in terms of average, maximum, minimum, and/or standard deviation saturation. In this manner, a large number of curves in a group can be reduced to a smaller number of curves characterizing that group.

Figures 4A, 4B:
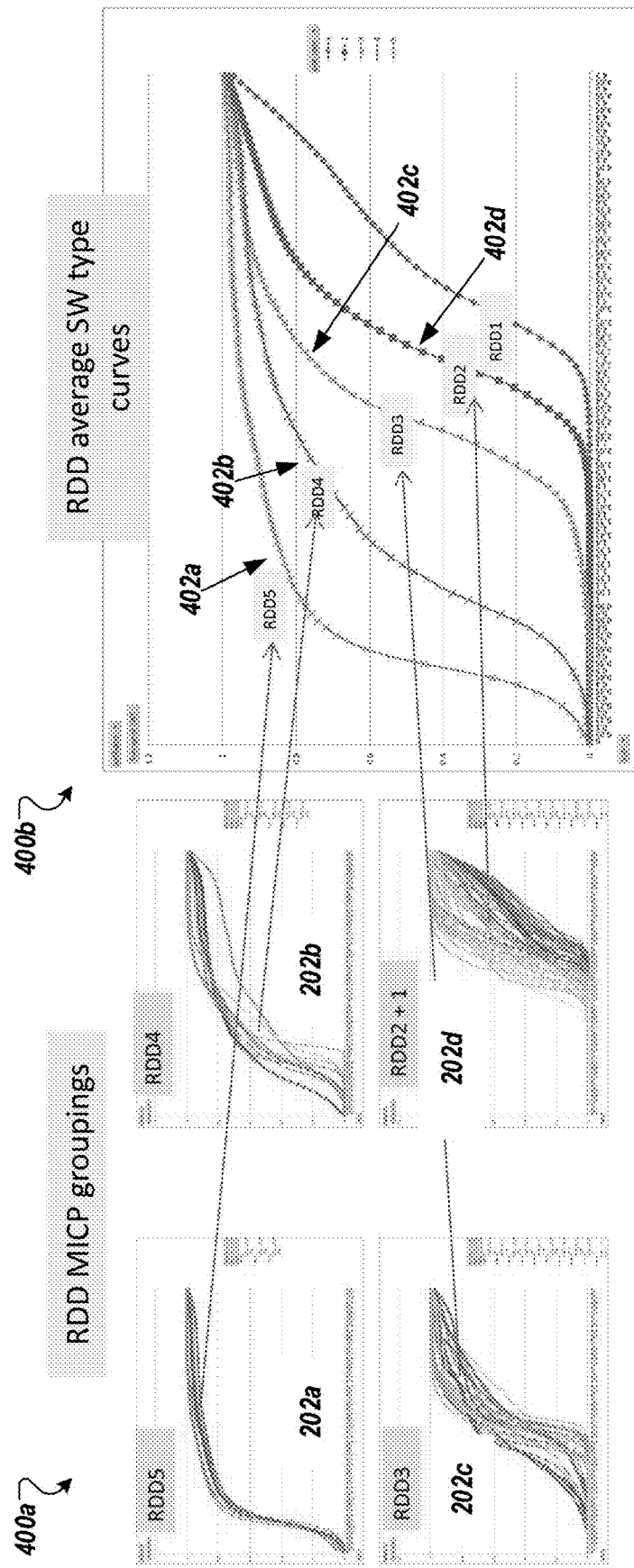
FIG. 4A illustrates a multiple plot with example curve groups, according to an implementation.
FIG. 4B shows example Capillary Pressure Type curves of the average of each curve group, according to an implementation.

Turning to FIGS. 4A-B, FIG. 4A illustrates a multiple plot 400a with example curve groups 202a-d, and FIG. 4B shows example CPT curves 402a-d of the average of each respective curve group 202a-d, according to an implementation. For example, average CPT curve 402a is generated by averaging of all of the individual curves in curve group 202a. In a similar manner, other CPT curves can be generated from the standard deviation, maximum, and/or minimum of the curves within a group.

Figure 5:
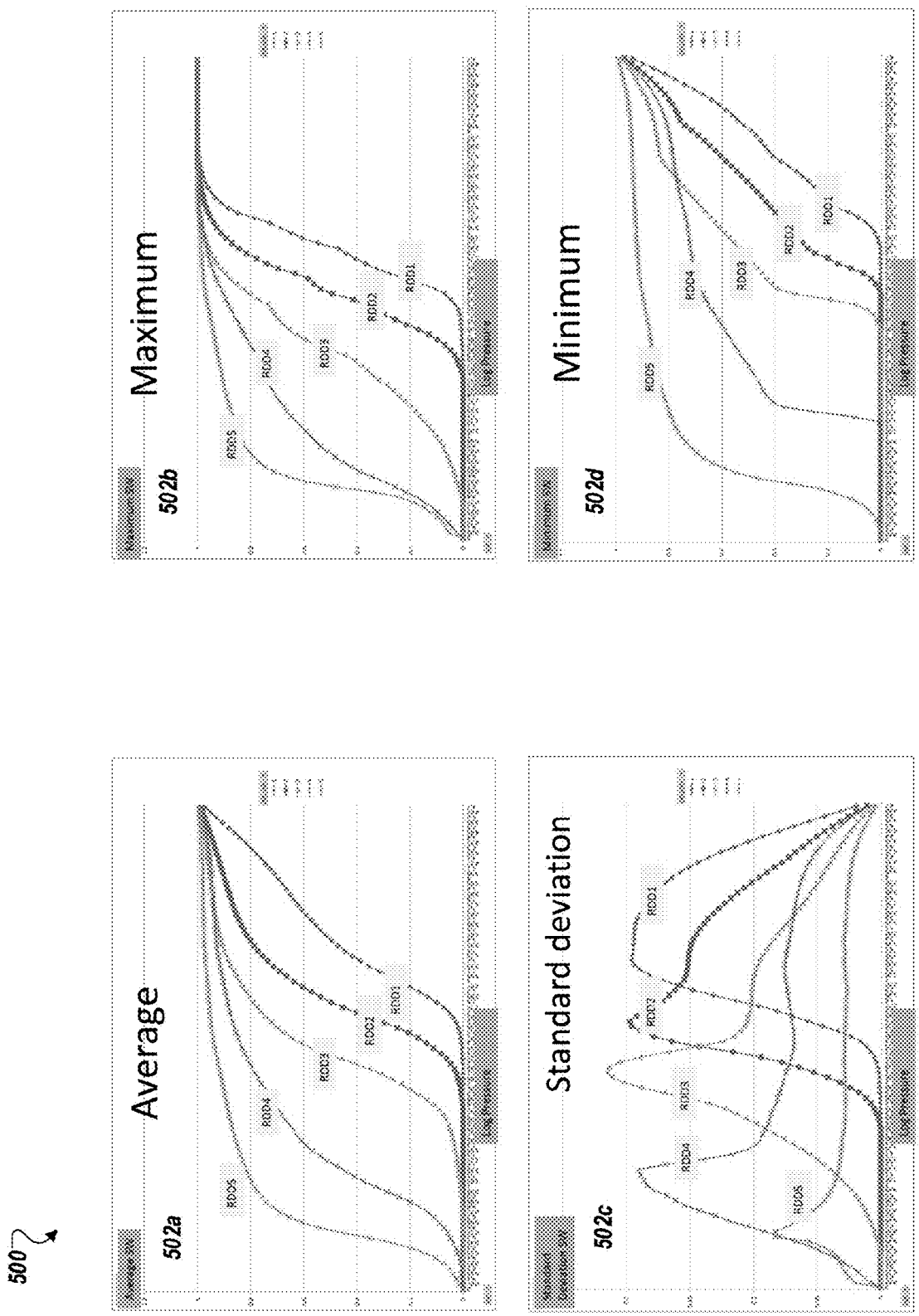
FIG. 5 illustrates plots of example Capillary Pressure Type curves for multiple groups, according to an implementation.

Turning to FIG. 5, FIG. 5 illustrates plots 502a-d of example CPT curves for multiple groups, according to an implementation. As shown in FIG. 5, plot 502a shows example average CPT curves for multiple groups as discussed previously for FIG. 4B. Plot 502b shows example maximum CPT curves for multiple groups, each maximum CPT curve generated by taking the maximum saturation value over all curves in the corresponding group at each pressure. Plot 502c shows example standard deviation CPT curves for multiple groups, each standard deviation CPT curve generated by taking the standard deviation over all curves in the corresponding group. Plot 502d shows example minimum CPT curves for multiple groups, each minimum CPT curve generated by taking the minimum saturation value of all curves in the corresponding group at each pressure. These are examples, and other CPT curves can be generated using other techniques. In this manner, each group can have a set of associated CPT curves. Returning to FIG. 1, from 106, method 100 proceeds to 108.

At 108, log data from a core is processed to identify RDCF within the log data. In some cases, the data corresponding to one or more RDCFs can be extracted directly from the log data. In some cases, the data corresponding to one or more RDCFs is processed after extraction from the log data. For example, log data can include clay and/or shale volume. As another example, elemental spectroscopy techniques can be used to predict mineral composition. One such technique used widely is the Multimin probabilistic analysis technique that uses a mineral model and measured physical characteristics within the log to predict the mineral compositions in the log. For example, if the minerals input to the model are representative of the minerals present in the formation and the physical characteristics of the minerals are measured by the logs, then the resultant predicted mineral log can represent the minerals in the formation. If, for example, the primary RDCF is one of the minerals present in the predicted mineral log, then this technique can provide a correlation between the core capillary data and log-based data.

Figure 6:
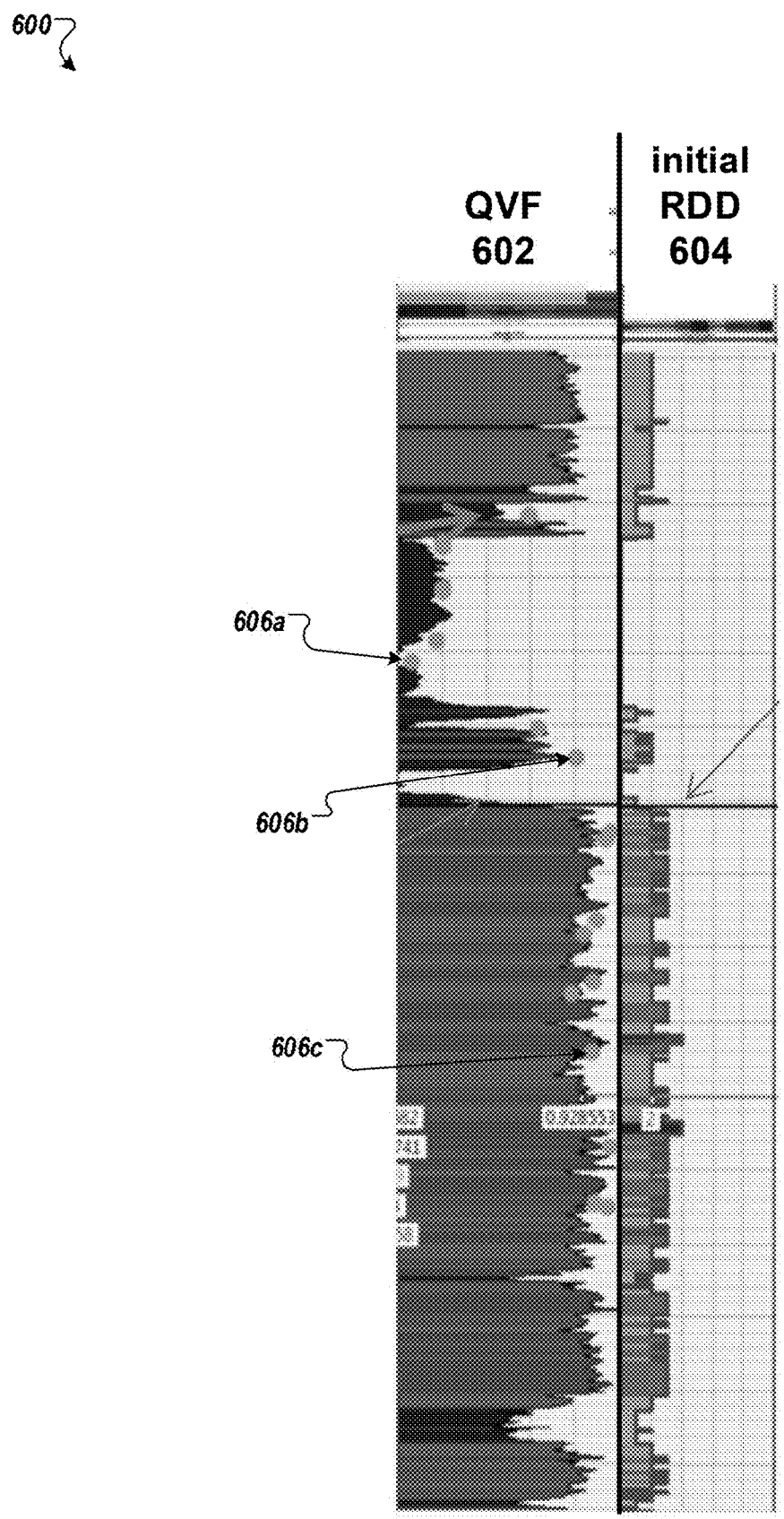
FIG. 6 illustrates example log data that can be generated using a Multimin technique, according to an implementation.

Turning to FIG. 6, FIG. 6 illustrates example log data 600 that can be generated using a technique like the Multimin technique described above, according to an implementation. In FIG. 6, data column 602 shows the Quartz Volume Factor (QVF) calculated using Multimin analysis from log data. In this example, the QVF data in data column 602 corresponds to the primary RDCF.

The quartz volume fraction measured using the quantitative mineral analysis from the core data set can correlate closely with the Multimin QVF analysis data for the well, shown by green points in data column 602. For clarity, a selection of core sample points 606a-c have been labeled. In some cases, the Multimin QVF data can be scaled to the total rock fabric to more closely correlate with the core data set. In some cases, log mineral volume fractions (MVF) can be referenced to the total rock volume (TRV). Core analysis data can be referenced to the total mineral volume (TMV). These volume fractions are different because the log MVF also includes the porosity volume. Thus, the TRV fractions can be converted to the TMV system by eliminating the porosity fraction. For example, this can be accomplished with the following equation:

$$MVF(TMV)=MVF(TRV)/(1-\text{total porosity})$$

This conversion can ensure that the mineral volumes are independent of the porosity and only representative of the true rock fragment. Returning to FIG. 1, from 108, method 100 proceeds to 110.

At 110, cut-offs are applied to the log-based RDCF data (e.g., data column 602) to derive an initial RDD log. The cut-offs, for example, can be ranges of RDCF that are associated with RDDs as determined from core analysis. The range of cut-offs can be based on the core RDD groupings compared with the RDCF. In some cases, porosity data or other data can also be used to generate an initial RDD log. In this manner, the same RDDs observed in the core can be associated with the corresponding log-based RDCF data.

Turning back to FIG. 6, data column 604 shows an initial RDD log after applying suitable cut-offs to the log-based RDCF data of data column 602. In data column 604, different colored regions represent different RDDs (e.g., RDD1, RDD2, RDD3, etc.). In the example shown in FIG. 6, only the poor reservoir quality RDD groupings are shown (i.e., RDD1, RDD2, and RDD3) where QVF is generally less than 95%. Returning to FIG. 1, from 110, method 100 proceeds to 112.

At 112, the CPT curves are applied to the initial RDD log to obtain an initial saturation distribution model corresponding to the initial RDD. The CPT curves can be used to predict an initial statistical distribution of the saturation by comparing the log-derived RDD to the core-based RDD. In some cases, the laboratory capillary measurement pressure is converted to the equivalent reservoir pressure, in which the pressure conversion is based on the ratio of surface tension to the contact angle of the two systems. Based on a density difference of the two reservoir fluids, an equivalent height above the free water level can also be determined. The uncertainty in the initial saturation distribution is defined by the envelope of maximum and minimum saturations and standard deviation, as determined by the CPT curves.

Figures 7A, 7B:
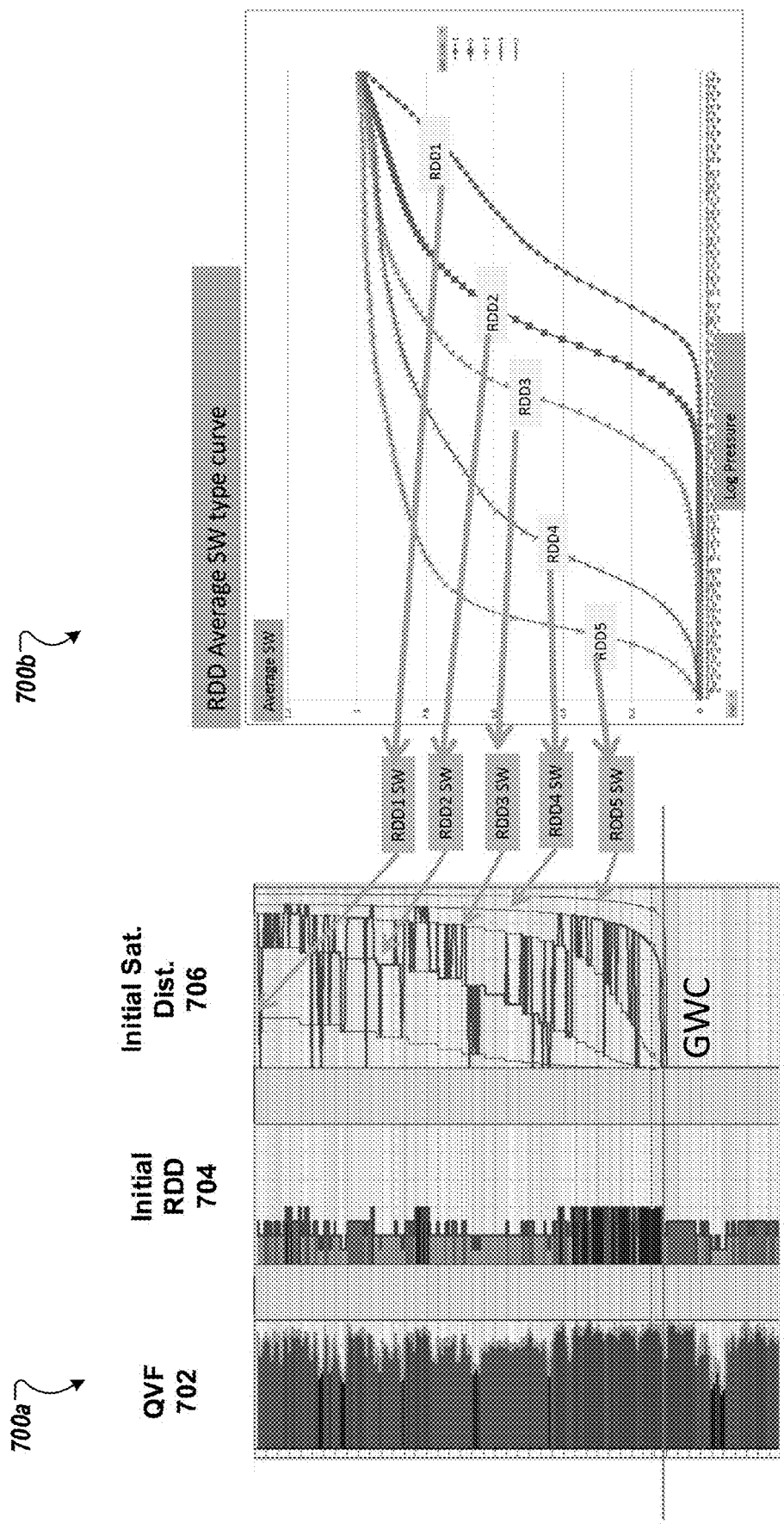
FIG. 7A illustrates an example plot of log data, according to an implementation.
FIG. 7B illustrates an example plot of average Capillary Pressure Type curves for each Reservoir Development Designation, according to an implementation.

Turning to FIG. 7A-B, FIG. 7A illustrates an example plot 700a of log data, including QVF data 702, an initial RDD log 704, and an initial saturation distribution 706, according to an implementation. FIG. 7B illustrates an example plot 700b of average CPT curves for each RDD. Based on the initial RDD log, the average CPT curve can be used to generate the initial saturation distribution. For example, for each data point in the log, the initial RDD determined for that point corresponds to a saturation predicted by the CPT curves associated with that RDD. In this manner, the initial RDD is combined with the capillary pressure CPT curves to derive a modelled saturation distribution. Returning to FIG. 1, from 112, method 100 proceeds to 114.

At 114, the CPT uncertainty envelope is compared with saturation measurements from the log. If the measured log saturations lie within the CPT curve envelope then the initial RDD log remains unchanged. If the measured log saturation for a log data point lies outside the CPT envelope, then the RDD for that data point is changed to improve agreement between the measured and modelled saturations. For example, an RDD can be changed to a "neighboring" RDD (e.g., RDD2 can be changed to RDD1 or RDD3). The output from this process is an "optimized" RDD.

The measured log saturations can provide a reference standard for the accuracy of the modelled saturations. The following describes how this initial saturation estimate compares with the measured log saturations.

Figure 8:
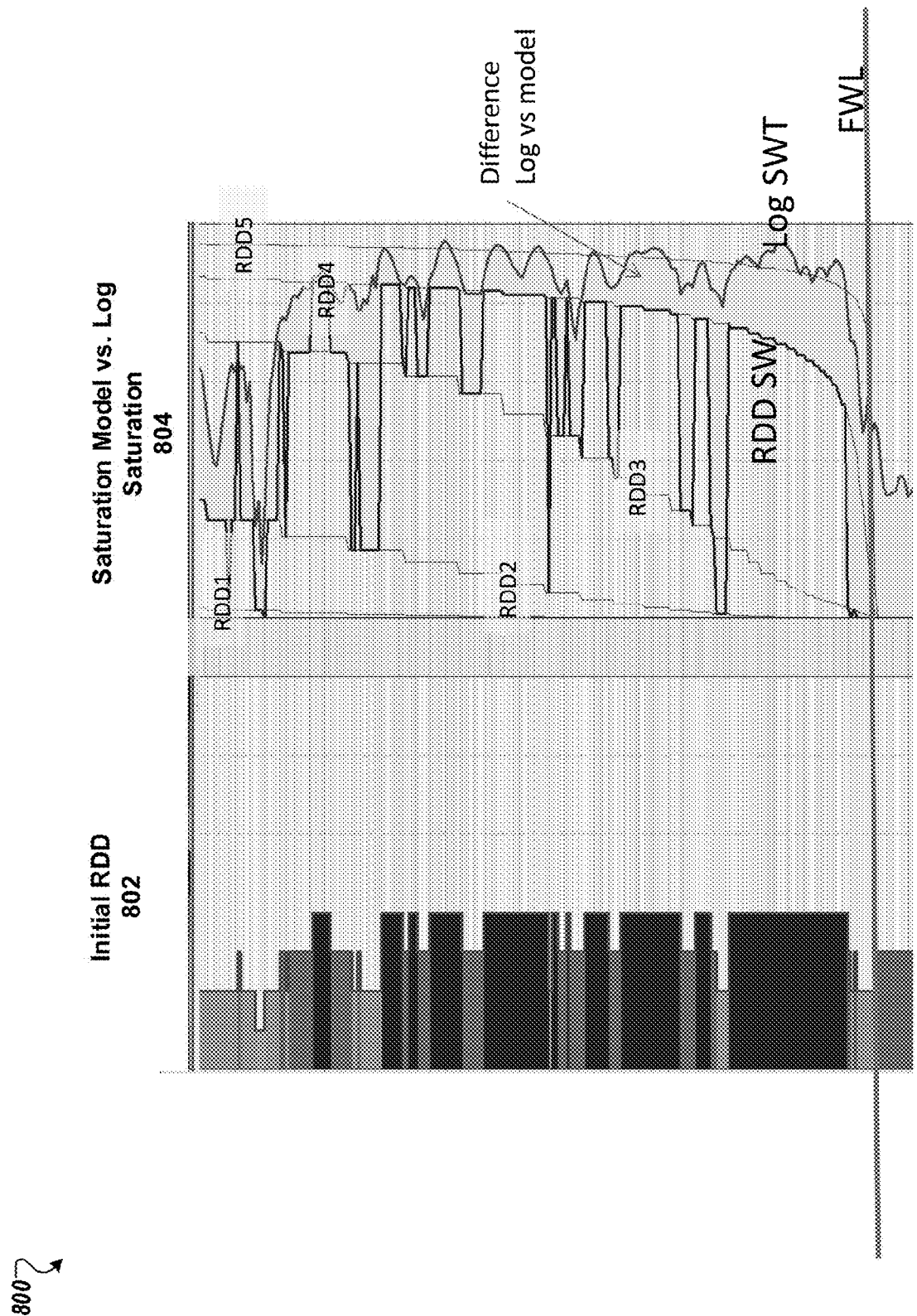
FIG. 8 illustrates a multiple plot of an example initial Reservoir Development Designation log and a plot of the measured log saturations vs. model saturations generated from the initial Reservoir Development Designation log, according to an implementation.

Turning to FIG. 8, FIG. 8 illustrates a multiple plot 800 of an example initial RDD log 802 and a plot 804 of the measured log saturations vs. model saturations generated from the initial RDD 802, according to an implementation. In plot 804, the blue line represents the modelled saturations and the red line represents the log saturations. The yellow region between the modelled and log saturations represents the difference between the two, indicating model inaccuracy.

The yellow region in plot 804 shows that the log water saturations are much lower than predicted by the initial saturation model. The difference can be caused by many variables such as uncertainty in the free water level (FWL), uncertainty in the log analysis, and/or other factors. Another possibility is that the difference could be representative of the scatter in the range of saturations associated with an RDD and/or that the uncertainty in the RDD allocation could mean that the RDD is not representative. In the example shown in FIG. 8, the FWL is well-defined and there are few indications to question the log saturation data. Thus, the discrepancy can be due to the range of saturations and/or the RDD allocation, for example. Returning to FIG. 1, from 114, method 100 proceeds to 116.

At 116, the modelled saturations are recalculated from the CPT curves for the optimized RDD. In some implementations, an Inverse Petrophysical Modeling technique can be used to recalculate the saturations. Inverse Petrophysical Modeling can use the full set of CPT curves to assess whether the saturation range associated with the defined RDD grouping is inconsistent with the measured log saturation. For example, if the log saturation is fully outside the range defined by the maximum or minimum saturation (from the appropriate CPT curves), then the RDD allocation can be changed. For example, if the log saturation is lower than the minimum CPT curve saturation for the group, then the RDD is increased, changing the RDD to a more likely candidate RDD.

Figure 9:
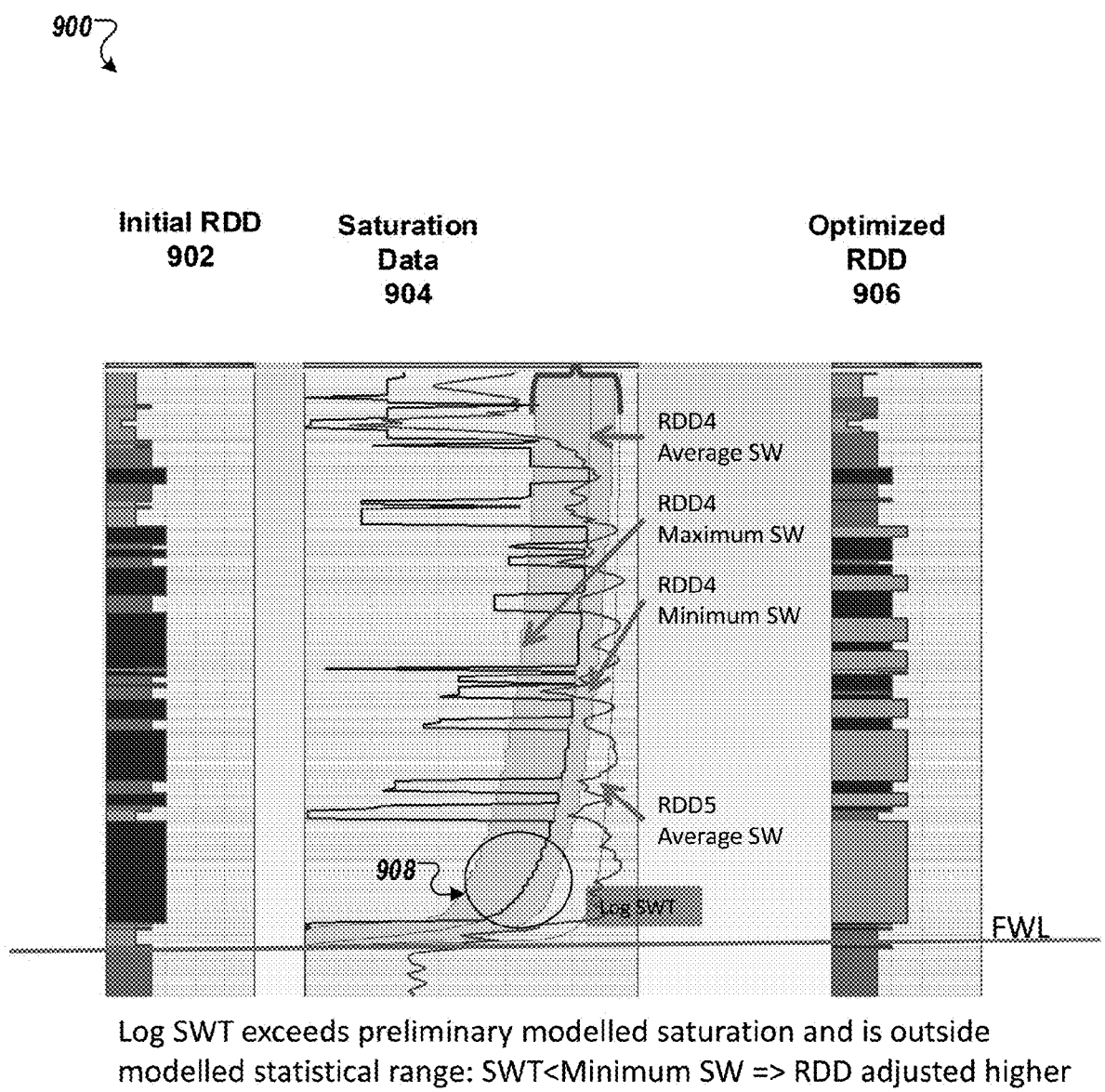
FIG. 9 illustrates a multiple plot of an example initial Reservoir Development Designation log, a plot of the measured log saturations and model saturations generated from the initial Reservoir Development Designation log, and a plot of the optimized Reservoir Development Designation after an Inverse Petrophysical Modeling technique has been applied, according to an implementation.

Turning to FIG. 9, FIG. 9 illustrates a multiple plot 900 of an example initial RDD log 902, a plot 904 of the measured log saturations and model saturations generated from the initial RDD log 902, and a plot 906 of the optimized RDD after an Inverse Petrophysical Modeling technique has been applied, according to an implementation. As an illustrative example, plot 904 shows the statistical range of RDD4 saturation as determined from the CPT curves and also shows the average RDD5 saturation. At some points in the log, the log saturation (shown in red in plot 904) has been assigned to RDD4, but the value of the log saturation is less than (to the right of) the minimum RDD4 saturation. In this case, the log saturation value is closer to the RDD5 statistical range than the RDD4 statistical range. Some example data points of this kind are highlighted in circle 908. The RDD for these points can be changed from RDD4 to RDD5, and the saturation model can be recalculated. In other cases, log data may retain the assigned RDD, or the RDD can be increased, decreased, or otherwise changed. In this manner, the saturation model can be changed to more accurately correspond to the log saturation data.

Figure 10:
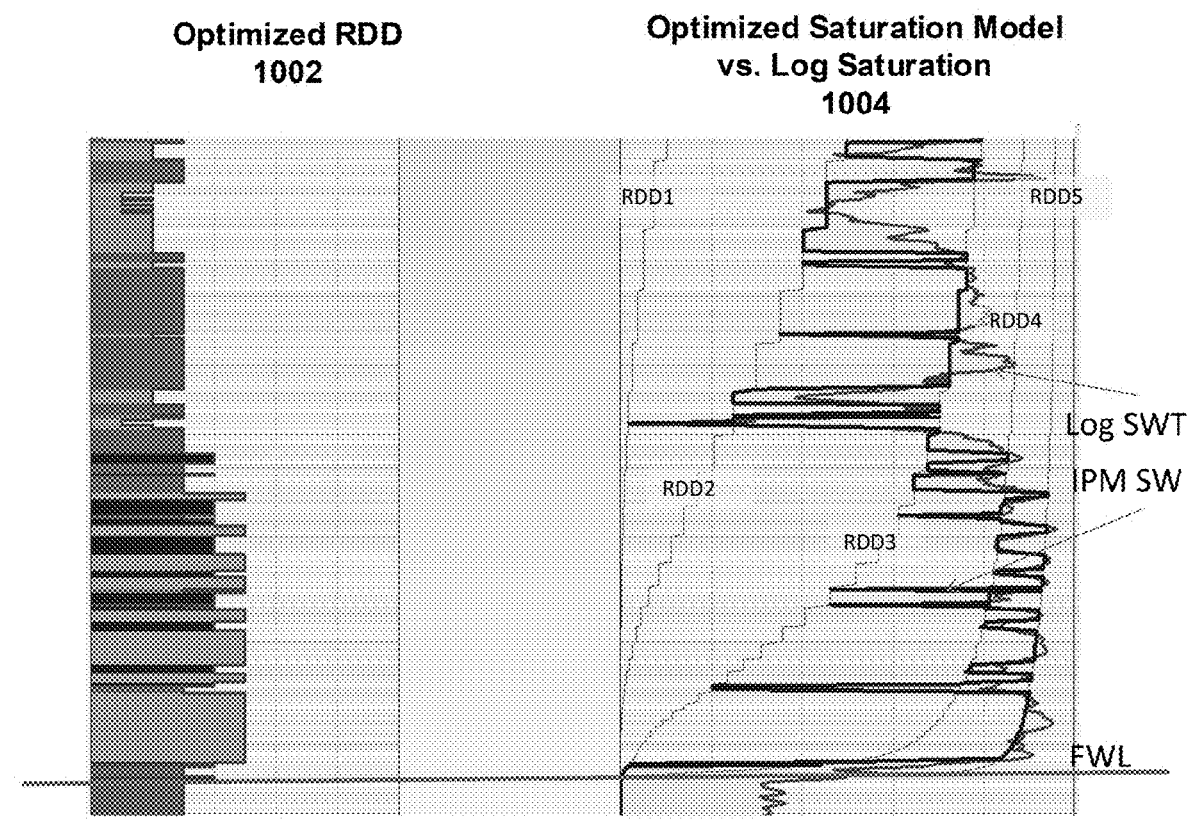
FIG. 10 illustrates a multiple plot of an example optimized Reservoir Development Designation log and a plot of the measured log saturations vs. optimized model saturations generated from the optimized Reservoir Development Designation log, according to an implementation.

Turning to FIG. 10, FIG. 10 illustrates a multiple plot 1000 of an example optimized RDD log 1002 and a plot 1004 of the measured log saturations vs. optimized model saturations generated from the optimized RDD log 1002, according to an implementation. In plot 1004, the blue line represents the optimized modelled saturations and the red line represents the log saturations. The yellow region between the modelled and log saturations represents the difference between the two, indicating model inaccuracy. As shown in FIG. 10, the difference between the optimized saturation model and the log saturations is significantly smaller than the comparison of log saturations with the initial saturation model shown in FIG. 8. In some implementations, the Inverse Petrophysical Modeling technique is repeatedly applied, generating increasingly accurate RDD logs and saturation models.

Figure 11:
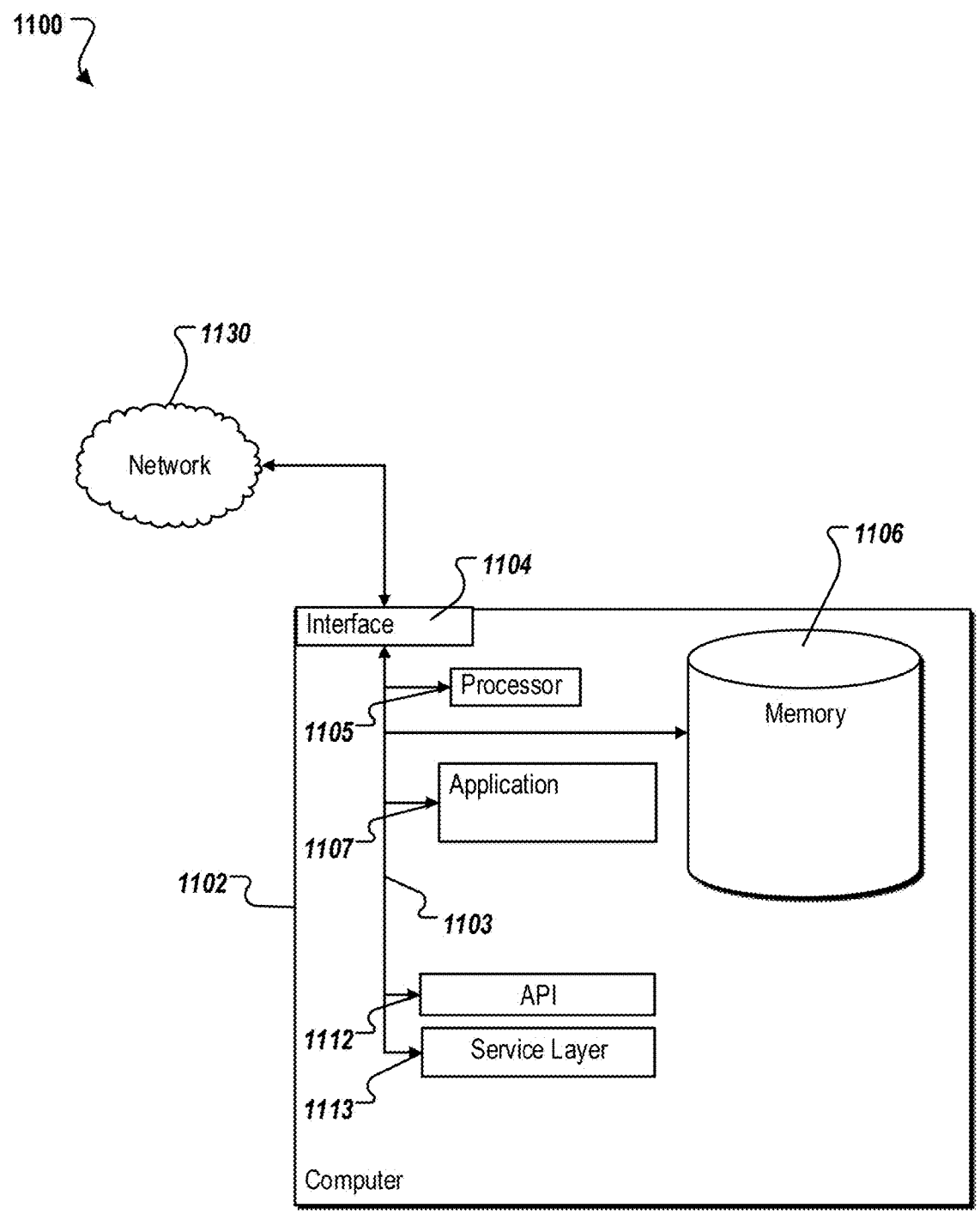
FIG. 11 is a block diagram of an example computer used to implement a saturation modeling and Reservoir Development Designation method, according to an implementation.

FIG. 11 is a block diagram 1100 of an exemplary computer 1102 used in the method 100 according to an implementation. The illustrated computer 1102 is intended to encompass any computing device such as a server, desktop computer, laptop/notebook computer, wireless data port, smart phone, personal data assistant (PDA), tablet computing device, one or more processors within these devices, or any other suitable processing device, including both physical and/or virtual instances of the computing device. Additionally, the computer 1102 may comprise a computer that includes an input device, such as a keypad, keyboard, touch screen, or other device that can accept user information, and an output device that conveys information associated with the operation of the computer 1102, including digital data, visual and/or audio information, or a GUI.

The computer 1102 can serve as a client, network component, a server, a database or other persistency, and/or any other component implementing method 100. The illustrated computer 1102 is communicably coupled with a network 1130. In some implementations, one or more components of the computer 1102 may be configured to operate within a cloud-computing-based environment.

At a high level, the computer 1102 is an electronic computing device operable to receive, transmit, process, store, or manage data and information associated with the method 100. According to some implementations, the computer 1102 may also include or be communicably coupled with an application server, e-mail server, web server, caching server, streaming data server, business intelligence (BI) server, and/or other server.

The computer 1102 can receive requests over network 1130 from a client application (e.g., executing on another computer 1102) and respond to the received requests by processing the said requests in an appropriate software application. In addition, requests may also be sent to the computer 1102 from internal users (e.g., from a command console or by other appropriate access method), external or third parties, other automated applications, as well as any other appropriate entities, individuals, systems, or computers.

Each of the components of the computer 1102 can communicate using a system bus 1103. In some implementations, any and/or all the components of the computer 1102, both hardware and/or software, may interface with each other and/or the interface 1104 over the system bus 1103 using an application programming interface (API) 1112 and/or a service layer 1113. The API 1112 may include specifications for routines, data structures, and object classes. The API 1112 may be either computer language-independent or -dependent and refer to a complete interface, a single function, or even a set of APIs. The service layer 1113 provides software services to the computer 1102. The functionality of the computer 1102 may be accessible for all service consumers using this service layer. Software services, such as those provided by the service layer 1113, provide reusable, defined business functionalities through a defined interface. For example, the interface may be software written in JAVA, C++, or other suitable language providing data in extensible markup language (XML) format or other suitable format. While illustrated as an integrated component of the computer 1102, alternative implementations may illustrate the API 1112 and/or the service layer 1113 as stand-alone components in relation to other components of the computer 1102. Moreover, any or all parts of the API 1112 and/or the service layer 1113 may be implemented as child or sub-modules of another software module, enterprise application, or hardware module without departing from the scope of this disclosure.

The computer 1102 includes an interface 1104. Although illustrated as a single interface 1104 in FIG. 3, two or more interfaces 1104 may be used according to particular needs, desires, or particular implementations of the computer 1102. The interface 1104 is used by the computer 1102 for communicating with other systems in a distributed environment connected to the network 1130 (whether illustrated or not). Generally, the interface 1104 comprises logic encoded in software and/or hardware in a suitable combination and operable to communicate with the network 1130. More specifically, the interface 1104 may comprise software supporting one or more communication protocols associated with communications such that the network 1130 or interface's hardware is operable to communicate physical signals within and outside of the computer 1102.

The computer 1102 includes a processor 1105. Although illustrated as a single processor 1105 in FIG. 3, two or more processors may be used according to particular needs, desires, or particular implementations of the computer 1102. Generally, the processor 1105 executes instructions and manipulates data to perform the operations of the computer 1102. Specifically, the processor 1105 executes the functionality for implementing a method such as method 100.

The computer 1102 also includes a memory 1106 that holds data for the computer 1102 and/or other components implementing method 100. Although illustrated as a single memory 1106 in FIG. 3, two or more memories may be used according to particular needs, desires, or particular implementations of the computer 1102 and/or the method 100. While memory 1106 is illustrated as an integral component of the computer 1102, in alternative implementations, memory 1106 can be external to the computer 1102.

The application 1107 is an algorithmic software engine providing functionality according to particular needs, desires, or particular implementations of the computer 1102 and/or the method 100, particularly with respect to functionality required for analyzing capillary pressure data, identifying RDD and RDCF, and modeling saturations. For example, application 1107 can serve as one or more components, modules, applications, etc. described with respect to FIGS. 1-10. Further, although illustrated as a single application 1107, the application 1107 may be implemented as multiple applications 1107 on the computer 1102. In addition, although illustrated as integral to the computer 1102, in alternative implementations, the application 1107 can be external to the computer 1102.

There may be any number of computers 1102 communicating over network 1130. Further, the terms "client," "user," and other appropriate terminology may be used interchangeably as appropriate without departing from the scope of this disclosure. Moreover, this disclosure contemplates that many users may use one computer 1102, or that one user may use multiple computers 1102.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refers to data processing hardware and encompasses all kinds of apparatus, devices, and machines for processing data, including by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically-erasable programmable read-only memory (EEPROM), and flash memory devices; magnetic disks, e.g., internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A computer-implemented method, comprising:
discriminating a multiple curve capillary pressure data set derived from a core sample into groups of similar curves representing similar pore structure groups;
identifying the primary reservoir development controlling factors (RDCFs) for each pore structure group;
creating a set of capillary pressure type curves for each pore structure group to statistically characterize saturation-pressure response for each pore structure group;
processing data from a log corresponding to the core sample to derive the identified RDCFs from the log data;
deriving a preliminary reservoir development designation log by applying cutoffs to the log-based RDCFs;
obtaining a preliminary saturation distribution equivalent to the preliminary reservoir development designation log by applying the set of capillary pressure type curves, wherein a capillary pressure type uncertainty envelope is defined by an envelope of maximum and minimum saturations and a standard deviation, as determined by the capillary pressure type curves;
comparing the capillary pressure type uncertainty envelope with saturation measurements from the log;
recalculating the preliminary saturation distribution from the average capillary pressure type curve to generate an optimized reservoir development designation; and
drilling one or more wells based on the optimized reservoir development designation.

2. The method of claim 1, wherein the capillary pressure data set is determined from a subset of core plug data selected from a pre-existing set of core plug data.

3. The method of claim 1, wherein a pore structure group is a group of curves associated with rock structures having similar porosities or permeabilities.

4. The method of claim 1, wherein the created capillary pressure type curves reduce the number curves characterizing each pore structure group using at least one of average, maximum, minimum, or standard deviation.

5. The method of claim 1, wherein a Multimin probabilistic analysis technique uses a mineral model and measured physical characteristics within the log to predict mineral compositions associated with the log.

6. The method of claim 1, comprising using an inverse petrophysical modeling technique with a full set of capillary pressure type curves to assess whether a saturation range associated with defined reservoir development designation groupings of the preliminary reservoir development designation log is inconsistent with the measured log saturation.

7. A non-transitory, computer-readable medium storing computer-readable instructions, the instructions executable by a computer and configured to:
discriminate a multiple curve capillary pressure data set derived from a core sample into groups of similar curves representing similar pore structure groups;
identify the primary reservoir development controlling factors (RDCFs) for each pore structure group;
create a set of capillary pressure type curves for each pore structure group to statistically characterize saturation-pressure response for each pore structure group;
process data from a log corresponding to the core sample to derive the identified RDCFs from the log data;
derive a preliminary reservoir development designation log by applying cutoffs to the log-based RDCFs;
obtain a preliminary saturation distribution equivalent to the preliminary reservoir development designation log by applying the capillary pressure type curves, wherein a capillary pressure type uncertainty envelope is defined by an envelope of maximum and minimum saturations and a standard deviation, as determined by the capillary pressure type curves;
compare the capillary pressure type uncertainty envelope with saturation measurements from the log;
recalculate the preliminary saturation distribution from the average capillary pressure type curve to generate an optimized reservoir development designation; and
causing one or more drilling tools to drill one or more wells based on the optimized reservoir development designation.

8. The non-transitory, computer-readable medium of claim 7, wherein the capillary pressure data set is determined from a subset of core plug data selected from a pre-existing set of core plug data.

9. The non-transitory, computer-readable medium of claim 7, wherein a pore structure group is a group of curves associated with rock structures having similar porosities or permeabilities.

10. The non-transitory, computer-readable medium of claim 7, wherein the created capillary pressure type curves reduce the number curves characterizing each pore structure group using at least one of average, maximum, minimum, or standard deviation.

11. The non-transitory, computer-readable medium of claim 7, wherein a Multimin probabilistic analysis technique uses a mineral model and measured physical characteristics within the log to predict mineral compositions associated with the log.

12. The non-transitory, computer-readable medium of claim 7, comprising instructions to use an inverse petrophysical modeling technique with a full set of capillary pressure type curves to assess whether a saturation range associated with defined reservoir development designation groupings of the preliminary reservoir development designation log is inconsistent with the measured log saturation.

13. A system, comprising:
a memory;
at least one hardware processor interoperably coupled with the memory and configured to:
discriminate a multiple curve capillary pressure data set derived from a core sample into groups of similar curves representing similar pore structure groups, wherein a pore structure group is a group of curves associated with rock structures having similar porosities or permeabilities;
identify the primary reservoir development controlling factors (RDCFs) for each pore structure group;
create a set of capillary pressure type curves for each pore structure group to statistically characterize saturation-pressure response for each pore structure group;
process data from a log corresponding to the core sample to derive the identified RDCFs from the log data;
derive a preliminary reservoir development designation log by applying cutoffs to the log-based RDCFs;
obtain a preliminary saturation distribution equivalent to the preliminary reservoir development designation log by applying the capillary pressure type curves, wherein a capillary pressure type uncertainty envelope is defined by an envelope of maximum and minimum saturations and a standard deviation, as determined by the capillary pressure type curves;
compare the capillary pressure type uncertainty envelope with saturation measurements from the log;

recalculate the preliminary saturation distribution from the average capillary pressure type curve to generate an optimized reservoir development designation; and causing one or more drilling tools to drill one or more wells based on the optimized reservoir development designation.

14. The system of claim 13, wherein the capillary pressure data set is determined from a subset of core plug data selected from a pre-existing set of core plug data.

15. The system of claim 13, wherein the created capillary pressure type curves reduce the number curves characterizing each pore structure group using at least one of average, maximum, minimum, or standard deviation.

16. The system of claim 13, wherein a Multimin probabilistic analysis technique uses a mineral model and measured physical characteristics within the log to predict mineral compositions associated with the log.

17. The system of claim 13, configured to use an inverse petrophysical modeling technique with a full set of capillary pressure type curves to assess whether a saturation range associated with defined reservoir development designation groupings of the preliminary reservoir development designation log is inconsistent with the measured log saturation.

* * * * *